US00PP14637P29

(12) United States Plant Patent
Trees

(10) Patent No.: US PP14,637 P2
(45) Date of Patent: Mar. 23, 2004

(54) LANTANA PLANT NAMED 'BALUCPEACH'

(50) Latin Name: *Lantana camara*
Varietal Denomination: Balucpeach

(75) Inventor: Scott C. Trees, Arroyo Grande, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 17 days.

(21) Appl. No.: 10/329,859

(22) Filed: Dec. 26, 2002

(51) Int. Cl.[7] ..... A01H 5/00
(52) U.S. Cl. ..... Plt./227
(58) Field of Search ..... Plt./227

*Primary Examiner*—Kent Bell
(74) *Attorney, Agent, or Firm*—Wood, Phillips, Katz, Clark & Mortimer

(57) ABSTRACT

A new and distinct Lantana plant named 'Balucpeach', characterized by its peach colored florets, upright growth habit, and dark green foliage.

2 Drawing Sheets

Latin name of genus and species of plant claimed: *Lantana camara.*
Variety denomination: 'Balucpeach'.

BACKGROUND OF INVENTION

The present invention comprises a new and distinct Lantana plant, botanically known as *Lantana camara*, and hereinafter referred to by the cultivar name 'Balucpeach'.

The new cultivar was developed by the inventor in a controlled breeding program during 1999, at Arroyo Grande, Calif. The objective of the breeding program was the development of Lantana cultivars with a well-branched, compact habit, continuous flowering and dark green foliage.

The female (seed) parent of 'Balucpeach' was the commercially available Lantana variety 'Confetti' (not patented), characterized by its pink/yellow bi-colored flowers and upright growth habit. The male (pollen) parent of 'Balucpeach' was the commercially available Lantana variety 'New Red' (not patented), characterized by its upright habit and red flowers. 'Balucpeach' was selected in May 2000 as a single flowering plant from within the progeny of the above stated cross and was designated 18-1.

Asexual reproduction of the new cultivar at Arroyo Grande, Calif. and West Chicago, Ill. was carried out by the use of terminal stem cuttings has demonstrated that the characteristics of the new cultivar as herein described are firmly fixed and retained through successive generations of such asexual propagation.

SUMMARY OF INVENTION

It was found that the cultivar of the present invention:

(a) exhibits peach colored flowers, (b) forms dark green foliage, and (c) exhibits an upright mounded growth habit.

The new cultivar of the present invention can be compared to the commercially available Lantana variety, 'Pink Caprice'. In side-by-side comparison, plants of the new cultivar differ from plants of 'Pink Caprice'. It is found that the new cultivar has a more compact habit, slightly larger leaves and flowers of a lighter yellow color.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 7 weeks in a greenhouse at West Chicago, Ill.

DETAILED BOTANICAL DESCRIPTION

Figure 1:
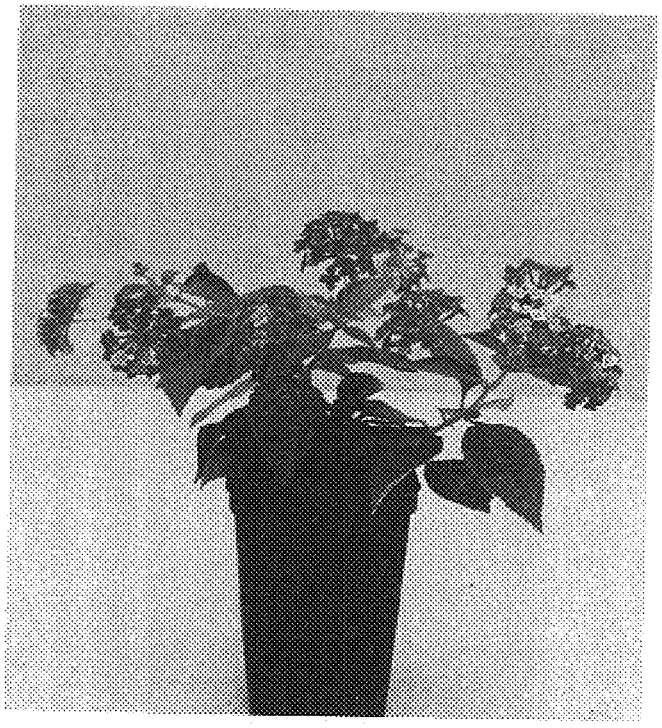
FIG. 1 illustrates the overall growth habit of the new cultivar.
Figure 2:
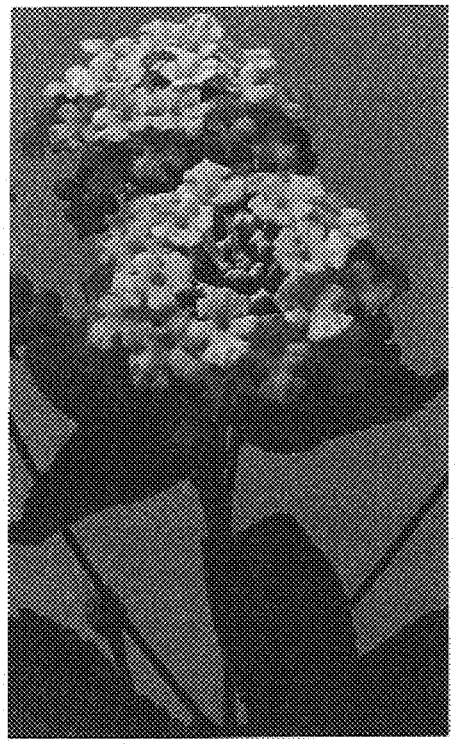
FIG. 2 illustrates a close up view of a single inflorescence of the new cultivar.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 15, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 7 weeks while utilizing a soilless growth medium and maintaining temperatures of approximately 75° to 85° F. (24° to 29° C.) during the day and approximately 62° to 68° F. (17° to 20° C.) during the night and light levels of 4,000 to 10,000 footcandles.

Classification:
*Botanical.*—*Lantana camara* cultivar 'Balucpeach'.
Parentage:
*Female parent.*—'Confetti'.
*Male parent.*—'New Red'.
Propagation:
*Type cutting.*—Terminal tip.
*Time to initiate roots.*—Approximately 14 to 21 days.
*Root description.*—Fibrous, branching.

Plant description:

*Habit of growth.*—Moderately vigorous. Pinching improves branching. A mature plant, 7 weeks after the planting of a rooted cutting, measures approximately 22 cm in height and approximately 20 cm in width with 2.5 main branches.

*Form.*—Upright, mounded.

*Branch.*—Square, approximately 17.8 cm in length and 3 mm in diameter, with moderate amount of long stiff hairs. Color is 144B. Internode length at middle of stem is approximately 4.8 cm.

*Foliage.*—Leaves are opposite, ovate with serrate/crenate margin, acute apex and attenuate base. Upper surface is rugose and densely covered with short, stiff hairs. Lower surface is moderately covered with short stiff hairs. Leaf length is approximately 8.1 cm and width is approximately 4.9 cm. Upper surface of mature foliage is 137A and lower surface is 137C. Upper and lower surfaces have pinnate-reticulate venation. Color of venation on upper surface is 144C. Color of venation on lower surface is 145C. Petiole surface is moderately covered with stiff hairs of moderate length, length is approximately 1.5 cm, diameter is approximately 2 mm and color is 145C.

Flowering description:

*Flowering habit.*—Freely flowering.

*Natural flowering season.*—Year round in greenhouse environment and spring through autumn in outdoor garden.

Inflorescence description:

*Shape.*—Spherical.

*Size.*—Approximately 2.6 cm in length and approximately 4.5 cm in diameter with approximately 30 fully open florets at any one time. Each floret is subtended by a single bract.

*Bract.*—Shape: Lanceolate. Length: Approximately 8 mm. Width: Approximately 1 mm. Apex: Acute. Margin: Entire. Texture: Both surfaces are moderately pubescent. Upper surface color: 144C. Lower surface color: 137C.

*Peduncle.*—Length: Approximately 6.8 cm. Diameter: Approximately 1 mm. Aspect: At acute angle to branch. Texture: Pubescent with short stiff hairs. Color: 144B.

Floret description:

*Fragrance.*—Light.

*Shape.*—Round.

*Aspect.*—Convex.

*Bud.*—Square, pillow shaped, approximately 4 mm in width and 3 mm in depth and 24D in color.

*Petals.*—Five, non-overlapping, fused at base forming corolla tube. Length: Approximately 7 mm. Width: Approximately 7 mm. Texture of upper surface: Glabrous. Texture of lower surface: Moderately pubescent with of hairs of 34B.

*Corolla.*—Diameter is approximately 1.2 cm. Petal color when fully open, the upper surface is 47C at margin 44B in center; 23A around tube opening. Color of lower surface is 8D.

*Corolla tube.*—Length is approximately 1.2 cm, diameter at tube opening is approximately 1 mm, diameter at base is approximately 1 mm. Outside of tube is densely covered with short hairs of 34B. Color of outer surface: 8C at base; 31A in center and 8C at apex. Inner surface of tube is smooth except for hairs around opening. Color of inner surface: 34D.

*Calyx.*—Tubular, formed by 5 fused sepals with acute tips. Length: Approximately 1 cm. Diameter: Approximately 3 mm.

*Reproductive organs.*—There are 4 stamens fused to the corolla tube. The anther length is less than 1 mm and the color is 200A. Pollen is moderate and 12C in color. There is one pistil, 4 mm in length. The stigma shape is round, the length is less than 1 mm and the color is 12B. The style length is approximately 2 mm and the color is 8D. Ovary length is less than 1 mm and color is 144B.

Seed production: Seed production has not been observed.

Disease resistance: Resistance to pathogens has not been observed.

Hardiness zone: 'Balucpeach' is hardy in zones nine (9) and above.

I claim:

1. A new and distinct *Lantana camara* plant named 'Balucpeach' substantially as herein shown and described, which:

(a) exhibits peach colored flowers, (b) forms dark green foliage, and (c) exhibits an upright growth habit.

* * * * *